US012661500B2

(12) United States Patent
Bakker et al.

(10) Patent No.: US 12,661,500 B2
(45) Date of Patent: Jun. 23, 2026

(54) MEDICAL ELECTRODE AND ARRANGEMENT THEREOF

(71) Applicant: INBRAIN NEUROELECTRONICS SL, Barcelona (ES)

(72) Inventors: Bert Bakker, Wijk en Aalburg (NL); José Antonio Garrido Ariza, Sant Just Desvern (ES)

(73) Assignee: INBRAIN NEUROELECTRONICS SL, Barcelona (ES)

( * ) Notice: Subject to any disclaimer, the term of this patent is extended or adjusted under 35 U.S.C. 154(b) by 250 days.

(21) Appl. No.: 18/566,047

(22) PCT Filed: Jun. 9, 2022

(86) PCT No.: PCT/EP2022/065655
§ 371 (c)(1),
(2) Date: Nov. 30, 2023

(87) PCT Pub. No.: WO2022/258739
PCT Pub. Date: Dec. 15, 2022

(65) Prior Publication Data
US 2024/0359003 A1     Oct. 31, 2024

(30) Foreign Application Priority Data
Jun. 9, 2021     (EP) ..................................... 21382511

(51) Int. Cl.
A61N 1/05          (2006.01)
(52) U.S. Cl.
CPC .................................. *A61N 1/0534* (2013.01)

(58) Field of Classification Search
CPC .. A61N 1/0534; A61N 1/0456; A61N 1/0472; A61N 1/0496; A61N 1/05;
(Continued)

(56) References Cited

U.S. PATENT DOCUMENTS

2016/0324435 A1* 11/2016 Kuzum ................ A61N 1/0551
2017/0080216 A1*  3/2017 Pham ................... A61N 1/0551
(Continued)

OTHER PUBLICATIONS

Kostarelos, K. et al., "Graphene in the Design and Engineering of Next-Generation Neural Interfaces," Advanced Materials, vol. 29, No. 42, Nov. 2017, Published Online Sep. 13, 2017, 7 pages.
(Continued)

*Primary Examiner* — Rex R Holmes
(74) *Attorney, Agent, or Firm* — McCoy Russell LLP

(57) ABSTRACT

The present invention relates to a medical electrode, including: a first layer made of a first material having a first electrochemical potential window, especially a first charge injection limit, and at least one second layer made of a second material having a second electrochemical potential window, especially a second charge injection limit, wherein the first layer and the second layer are located on a base substrate, wherein the second electrochemical potential window is lower than the first electrochemical potential window, and wherein the first layer is provided on top of the second layer and encapsulates the second layer, so that no electrical current directly flows from the second layer toward a target tissue.

17 Claims, 4 Drawing Sheets

(58) Field of Classification Search
CPC .... A61N 1/0529; A61N 1/0551; A61B 5/263;
A61B 2562/125
See application file for complete search history.

(56) References Cited

U.S. PATENT DOCUMENTS

| | | |
|---|---|---|
| 2018/0056057 A1 | 3/2018 | Kalita et al. |
| 2019/0321629 A1* | 10/2019 | Radivojevic ....... A61N 1/36014 |

OTHER PUBLICATIONS

ISA European Patent Office, International Search Report and Written Opinion Issued in Application No. PCT/EP2022/065655, Sep. 14, 2022, WIPO, 11 pages.

* cited by examiner

MEDICAL ELECTRODE AND ARRANGEMENT THEREOF

CROSS REFERENCE TO RELATED APPLICATIONS

The present application is a U.S. National Phase of International Application No. PCT/EP2022/065655 entitled "MEDICAL ELECTRODE AND ARRANGEMENT THEREOF," and filed on Jun. 9, 2022. International Application No. PCT/EP2022/065655 claims priority to European Patent Application No. 21382511.0 filed on Jun. 9, 2021. The entire contents of each of the above-listed applications are hereby incorporated by reference for all purposes.

TECHNICAL FIELD

The present invention belongs to the technical field of medical electrodes.

BACKGROUND AND SUMMARY

More specifically, the present invention refers to an electrode for use in a medical device, e.g., a neurostimulation device.

The electrode may be implantable.

Alternatively, the electrode may be non-implantable.

For instance, the electrode can be used to perform Deep Brain Simulation (DBS).

DBS is a neurosurgical procedure involving the use of implanted electrodes and electrical stimulation for the treatment of a neurological disorder.

When the electrode contacts a target living tissue, electrical currents are allowed to flow between the electrode and the target living tissue.

A medical electrode may include a first layer and at least one second layer, made of different materials. The first and second layers are placed on a base substrate. In case of electrodes using graphene as material is it know to have one base layer of metal for electrical interconnection and a second layer with graphene as electrode material. The graphene cane be reduced Graphene Oxide (rGO). An example of such medical electrode according to the prior art is shown in FIG. 1.

When an electrode includes two (or more) layers made of different materials, electrical currents from both layers flow toward a target living tissue subject to treatment.

The actual currents for each material depend on the impedance of that specific material.

Further, each material is characterized by a specific electrochemical potential window and, accordingly, charge density limit.

The electrochemical potential window defines a limit in terms of voltage that can drop at the material-tissue interface before the occurrence of electrode reactions and degradation of the material.

FIG. 2 shows an example of a known medical electrode including a first layer made of graphene on top of a second layer made of metal. The electrode interfaces a target living tissue.

During treatment, both layers contact the target living tissue. Accordingly, two different currents $I_G$ and $I_M$ are directed to and reach the target living tissue (FIG. 2). The currents $I_G$ and $I_M$ depend on the material-tissue interface impedance. Each of the materials has its own maximum current, which depends on the maximum electrochemical potential window for that specific material.

The overall electrochemical potential window for the electrode is defined by the material which first reaches the boundaries of its own electrochemical potential window.

In particular, when the maximum current is reached at one of the two or more materials at that specific maximum electrochemical potential window, then the overall maximum current is reached for the electrode (in the example of FIG. 2, $I_G+I_M$).

In case the electrochemical potential windows of the two or more materials differ significantly, e.g. by three orders of magnitude or more, the limitation opposed by the material having the lower electrochemical potential window may block the potential of the material having the higher electrochemical potential window, and is thus undesired.

Accordingly, it is desirable to prevent electrical current from directly flowing from the second layer (e.g. a metal layer) having the lower electrochemical potential window toward the target living tissue.

FIG. 3 shows a configuration where an electrically insulating layer, e.g. made of an electrically-insulating polymer material, is provided to prevent (or at least reduce) direct flow of electrical current from the second layer toward the target living tissue.

In particular, said electrically insulating layer covers the second layer and surrounds (e.g., in a "clamping" fashion) the first layer having the higher electrochemical potential window, while leaving said first layer exposed.

Although effective, however this known solution still shows some drawbacks.

In particular, it has been observed that electrically-insulating materials such has polymers are not always capable of properly attaching to the electrode layers or released under stress, so that water or bodily fluids may flow though spaces that exist between the first and second layers and the electrically insulating layer, thereby generating unwanted bypass paths permitting electrical current from the second layer to directly flow toward the target living tissue (as indicated by the arrow in FIG. 3).

Hence, there is the need for an improved solution capable of overcoming the above-mentioned drawbacks of the prior art.

In particular, it is an object of the present invention to provide a medical electrode capable of more effectively preventing the occurrence of a direct flow of electrical current from a second layer having a lower electrochemical potential window toward a target living tissue, which may hinder the potential of a first layer having a higher electrochemical potential window.

This object is achieved by the provision of a medical electrode according to claim 1.

According to the invention, a medical electrode includes:

a first layer made of a first material having a first electrochemical potential window, especially a first charge injection limit, and at least a second layer made of a second material having a second electrochemical potential window, especially a second charge injection limit, wherein the first layer and the second layer are located on a base substrate, wherein the second electrochemical potential window is lower than the first electrochemical potential window, and wherein the first layer is provided on top of the second layer and encapsulates the second layer, so that no electrical current directly flows from the second layer toward a target tissue.

The present invention provides a medical electrode.

The medical electrode can be used in a medical device, e.g., a neurostimulation device.

The electrode includes a first layer made of a first material.

The first material is characterized by a first electrochemical potential window.

There is also at least one second layer, made of a second material.

The second material is characterized by a second electrochemical potential window, lower than the first electrochemical potential window.

The first layer and the second layer are located on a base substrate.

Preferably, the base substrate is made of a polymer material such as Polyimide or Liquid Crystal Polymer (LCP).

The first layer is provided on top of the second layer.

The first layer encapsulates the second layer.

Accordingly, no electrical current is allowed to directly flow from the second layer having the lower electrochemical potential window toward a target living tissue.

The invention is based on the basic idea that, by encapsulating the second layer having the lower electrochemical potential window with the first layer having the higher electrochemical potential window, all currents necessarily need to pass through the first layer in order to reach the target living tissue, while no electrical current is allowed to directly flow from the second layer toward the target living tissue. Accordingly, blocking of the potential of the first layer having the higher electrochemical potential window can be largely avoided.

Advantageously, an electrically insulating layer made of an electrically insulating material may be provided, which covers the second layer.

The electrically insulating layer surrounds the first layer while leaving said layer exposed.

Accordingly, the first layer is capable of coming into contact with the target (living) tissue.

The electrically insulating layer provides for an improved electrical insulation, further reducing the risk of an undesired direct flow of electrical current from the second layer toward the target (living) tissue.

Advantageously, said electrical insulating layer is made of an electrically insulating polymer material.

The second layer can be made of metal.

The first layer can be made of graphene.

As an alternative, the first layer can be made of nanoporous reduced Graphene Oxide (rGO).

In such a case, it is preferable that an electrically conductive and porous, especially water permeable, additional layer is interposed between the first layer and the second layer.

In particular, when the first layer is made of a nanoporous material such as nanoporous rGO, water or bodily fluids may permeate the nanoporous material, trickle through the pores and eventually reach the second layer. This may generate an undesired interface between the second layer and the target living tissue, which may determine an unwanted direct flow of electrical current from the second layer toward the target (living) tissue.

The provision of said additional layer, which is electrically conductive but not permeable to water, allows to maintain electrical connection between the first and second layers, at the same time preventing water or other bodily fluids from permeating through the nanoporous first layer and reach the second layer. In particular, by having e.g. a (CVD) graphene with non-permeable layer on top of the metal will prevent direct contact of water or ions to the metal.

Advantageously, said electrically conductive and water permeable additional layer is made of graphene.

In particular, said electrically conductive and water permeable additional layer may include a single layer of graphene.

As an alternative, said electrically conductive and water permeable additional layer may include multiple layers of graphene.

The medical electrode can be implantable.

Alternatively, the medical electrode can be non-implantable.

The present invention further provides a medical electrode arrangement.

The medical electrode arrangement includes a plurality of medical electrodes as described above.

The medical electrode arrangement further includes a connecting track made of an electrically conductive material.

The connecting track is provided to electrically connect the plurality of electrodes to one another.

When a plurality of medical electrodes as described above is connected through the connecting track, it may occur that an undesired flow of electrical current flows from the second layer toward the target living tissue through said track.

To prevent this undesired occurrence, the connecting track is advantageously encapsulated in an electrically insulating material.

Accordingly, undesired flows of electrical current from the second layer toward the target living through the track can be largely avoided.

Said insulating material incapsulating the track may include a dielectric film.

Additionally or alternatively, said insulating material may include or be a polymer layer, especially a parylene layer or a polyimide layer or a silicone layer or the like.

Additionally or alternatively, said insulating material may include a ceramic layer.

The connecting track can be made of metal.

Also, the present invention provides a medical electrode arrangement according to a further embodiment.

The medical electrode arrangement includes a plurality of medical electrodes as described above.

The medical electrode arrangement further includes a connecting track made of an electrically conductive material.

The connecting track is provided to electrically connect the plurality of electrodes to one another.

When a plurality of medical electrodes as described above is connected through the connecting track, it may occur that an undesired flow of electrical current flows from the second layer toward the target living tissue through said track. In particular, it should be noted that the track material is or can be connected to the second layer. Further the track material can be made of the same material like the second layer.

To prevent this undesired occurrence, at least one interconnection layer can be provided and can be sandwiched between the insulating separation layer and the base substrate.

Said interconnection layer covers the connecting tracks.

At least one via is formed through, the second layer and the (third) interconnection track.

Said at least one via allows to establish electrical connection between the electrode and the connecting track.

In particular, a single electrically conductive e.g., metal via may be formed through, the second layer and the interconnection track. In particular, the first layer can cover the via completely. The via electrically connects to second layer and third layer, the interconnection layer.

It is further possible that the metal via (same material as second layer and interconnection track likely) electrically connects to second layer and third layer: the interconnection track located in the interconnection layer.

Alternatively, a plurality of vias may be formed through, the second layer and the interconnection track.

The connecting track is electrically conductive and can be made of metal.

BRIEF DESCRIPTION OF THE FIGURES

Further details and advantages of the present invention shall now be disclosed in connection with the drawings, where.

DETAILED DESCRIPTION

Figure 4:
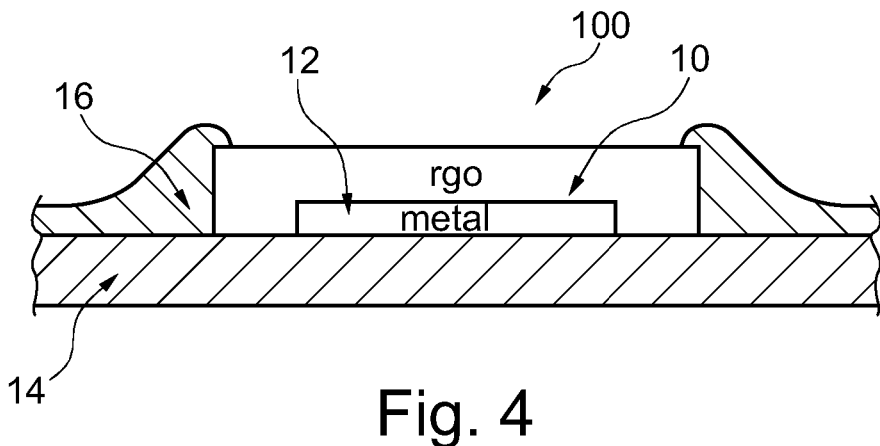
FIG. 4 is a front view of a medical electrode according to an embodiment of the present invention, including a first layer made of reduced Graphene Oxide (rGO) on top of a second layer made of metal.
Figure 5:
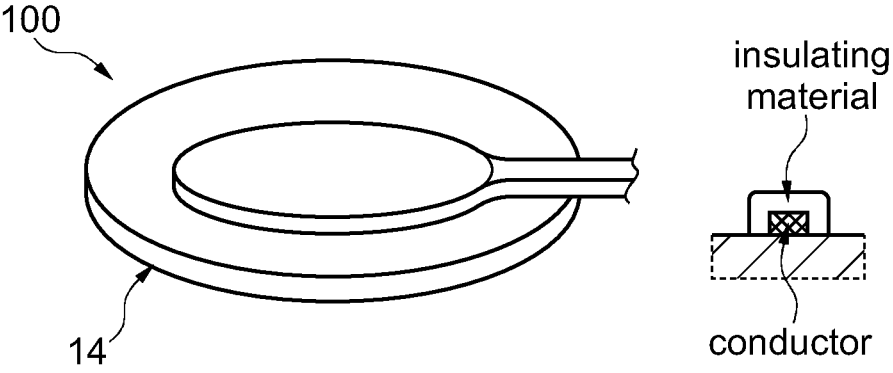
FIG. 5 is a perspective view of the electrode of FIG. 4.

FIGS. 4-5 show a medical electrode 100 according to an embodiment of the present invention.

The medical electrode includes a first layer 10 made of a first material having a first electrochemical potential window.

In the shown embodiment, the first layer 10 is made of nanoporous reduced Graphene Oxide (rGO) (FIG. 4).

Not shown is that the first layer can be made of graphene or other suitable material.

The medical electrode 100 further includes a second layer 12 made of a second material having a second electrochemical potential window, lower than the first electrochemical potential window of the first layer 10.

In the shown embodiment, the second layer 12 is made of metal (FIG. 4).

The first layer 10 and the second layer 12 are located on a base substrate 14.

The base substrate 14 may include a polymer material such as Polyimide or Liquid Crystal Polymer (LCP), or any other suitable material.

The first layer 10 is placed on top of the second layer 12.

The first layer 10 encapsulates the second layer 12.

Accordingly, all currents necessarily need to pass through the first layer 10 in order to reach a target living tissue (not shown), while no electrical current is allowed to directly flow from the second layer 12 toward the target living tissue.

Accordingly, blocking of the potential of the first layer 10 having the higher electrochemical potential window can be largely avoided.

In the shown embodiment (FIG. 4), an electrically insulating layer 16 made of an electrically insulating material is provided, covering the second layer 12.

The electrically insulating layer 16 is surrounds the first layer 10 (e.g., in a "crimping" fashion), while leaving the first layer 10 exposed.

Accordingly, the first layer 10 is allowed to come into contact with the target living tissue.

In the present embodiment, the electrically insulating layer 16 is made of an electrically insulating polymer material.

Figure 1:
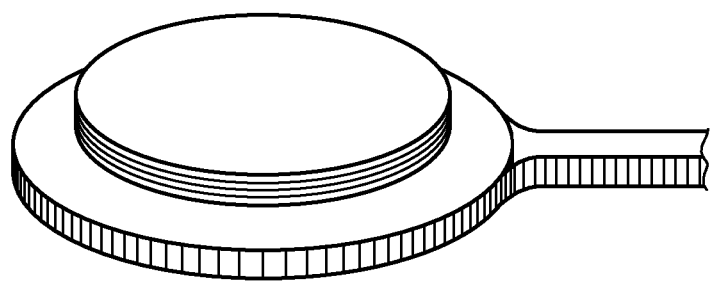
FIG. 1 is a perspective view of a medical electrode including a first layer made of a first material and a second layer made of a second material, according to the prior art.
Figure 2:
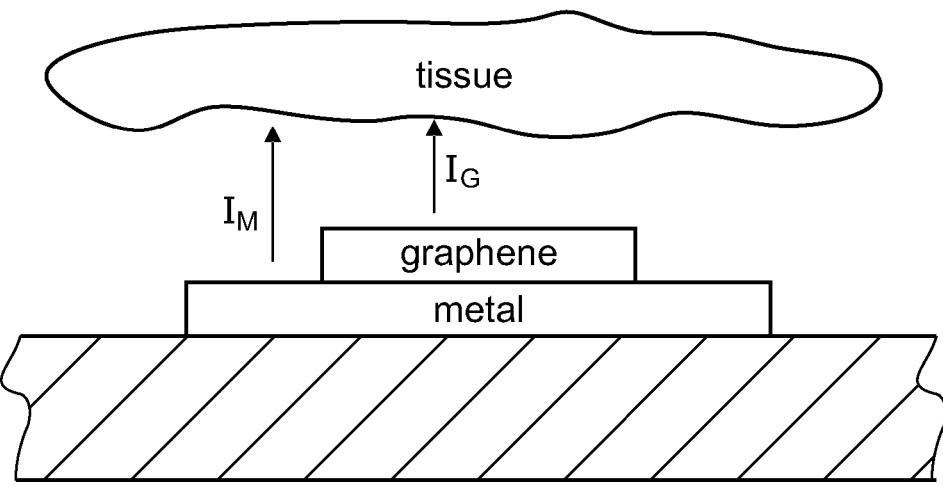
FIG. 2 is a front view of a medical electrode according to the prior art interfacing with a target living tissue, said electrode including a first layer made of graphene on top of a second layer made of metal.
Figure 3:
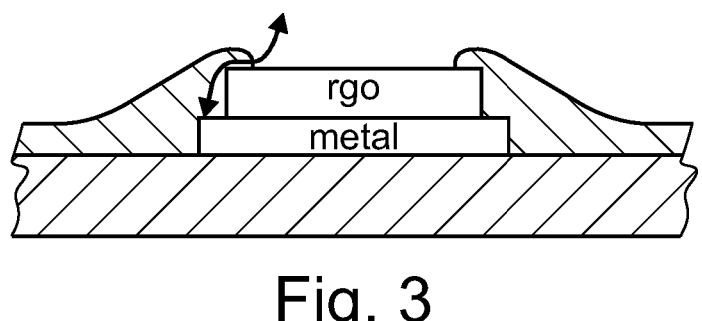
FIG. 3 is a front view of a medical electrode similar to the one of FIG. 2, but where an electrically insulating layer is provided to cover the second layer while leaving the first layer exposed. The arrow shows an undesired direct flow of electrical current from the second layer toward the target living tissue.
Figure 6:
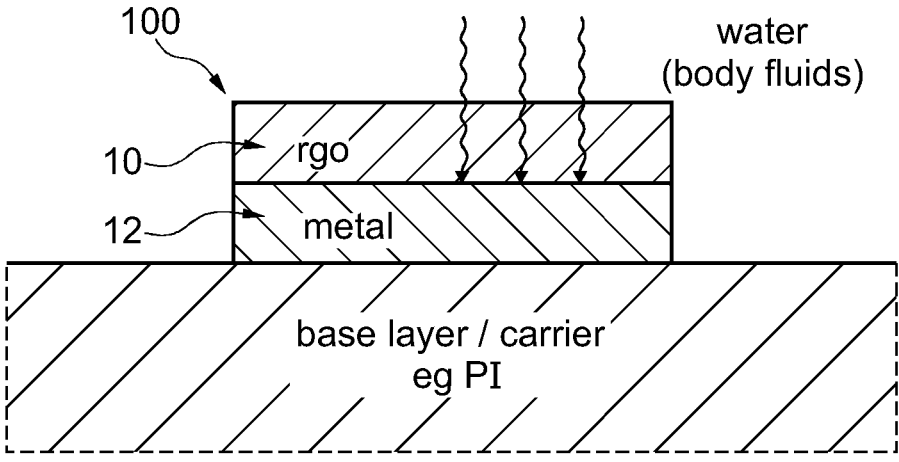
FIG. 6 shows a condition where water or bodily fluids permeate through the first layer (here, a nanoporous rGO layer), and eventually reach the second layer (here, a metal layer)

Since the first layer 10 is made of a nanoporous material (nanoporous rGO), water or bodily fluids may permeate through the first layer 10 and eventually reach the second layer 12 as shown in FIG. 6. This may generate an undesired interface between the second layer 12 and the target living tissue, which may determine an unwanted direct flow of electrical current from the second layer 12 toward the target living tissue (see the arrow in FIG. 3).

Figure 7:
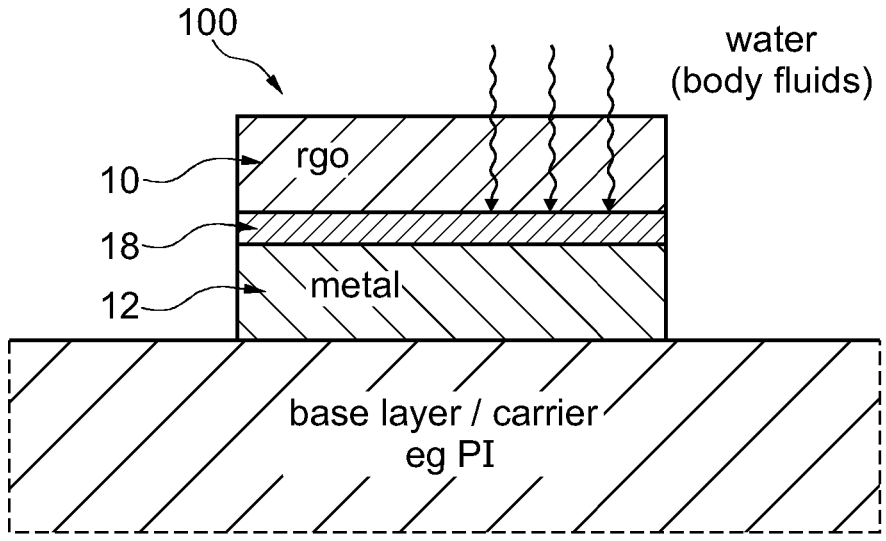
FIG. 7 is a front view of a medical electrode similar to the one of FIG. 6, but where an electrically conductive and water non-permeable additional layer (e.g. made of graphene) is interposed between the first electrode layer and the second electrode layer.

To prevent this occurrence, an electrically conductive and water non-permeable additional layer 18 is interposed between the first layer 10 and the second layer 12, as shown in FIG. 7.

In the shown embodiment, the electrically conductive and water permeable additional layer 18 is made of graphene.

For instance, the additional layer 18 may include a single layer of graphene.

Alternatively, the additional layer 18 may include multiple layers of graphene.

Since the electrode layer 18 is electrically conductive but non-permeable to water, the electrical connection between the first layer 10 and the second layer 12 can be maintained while water or other bodily fluids are prevented from permeating through the nanoporous first layer 10 and eventually being blocked to reach the second layer 12.

The medical electrode 100 can be implantable.

Alternatively, the medical electrode 100 can be non-implantable.

The present invention further provides a medical electrode arrangement (not shown).

The medical electrode arrangement includes a plurality of medical electrodes 100 according to the invention, the features of which have been described in detail in the foregoing.

The medical electrode arrangement further includes a connecting track made of an electrically conductive material, for electrically connecting said plurality of medical electrodes 100.

In the present embodiment, said connecting track is made of metal.

When a plurality of electrodes 100 are electrically connected to one another through the track in order to form the electrode arrangement, there is the possibility that an undesired flow of electrical current flows from the second layer 12, incapsulated by the first layer 10, toward the target living tissue through the track.

To prevent this undesired occurrence, the connecting track is encapsulated in an electrically insulating material.

Accordingly, undesired flow of electrical current from the second layer 12 toward the target living tissue through the track can be largely avoided.

The insulating material may include a dielectric film, a ceramic layer, a parylene layer, or a combination thereof.

Figure 8:
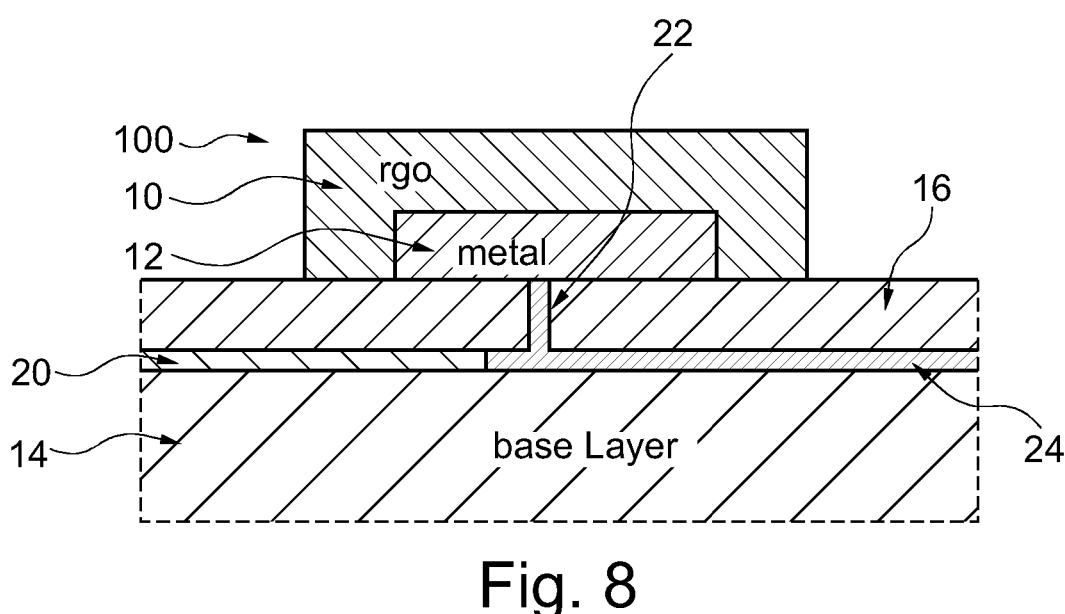
FIG. 8 shows a detail of a medical electrode in an electrode arrangement according to an embodiment of the present invention, where an interconnection layer is sandwiched between the base layer, and the insulation separation layer, and a via is formed through the insulation separation layer electrically interconnecting, the second layer and the interconnection track located in the interconnection layer.
Figure 9:
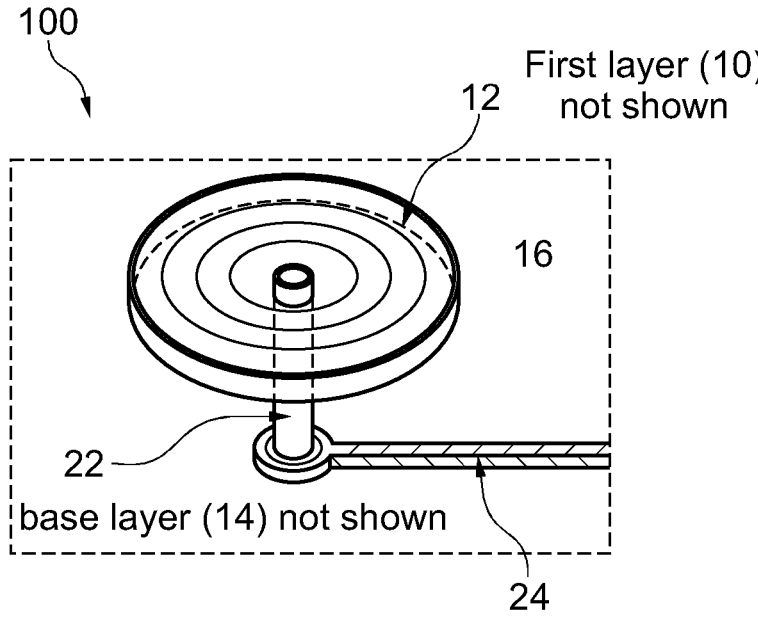
FIG. 9 shows a perspective view of the electrode of FIG. 8.

FIGS. 8-9 show a detail of an electrode arrangement according to a further embodiment of the present invention.

The medical electrode arrangement includes a plurality of medical electrodes 100 according to the invention, the features of which have been described in detail in the foregoing.

The medical electrode arrangement further includes a connecting track made of an electrically conductive material, for electrically connecting said plurality of medical electrodes 100.

In the present embodiment, said connecting track is made of metal.

When a plurality of electrodes 100 are electrically connected to one another through the track in order to form the electrode arrangement, there is the possibility that an undesired flow of electrical current flows from the second layer 12, incapsulated by the first layer 10, toward the target living tissue through the track.

To prevent this undesired occurrence, at least one interconnection layer 20 made of an electrically insulating material is encapsulated between insulation separation layer 26 and the base substrate 14 (FIG. 8).

The interconnection layer 20 covers the electrically conductive connecting tracks 24.

At least one electrically conductive via 22 is passing through the insulation interconnection layer 20 and electrically interconnecting the second layer 12 and the interconnection track 24, effectively connecting the electrode 100 to the connecting track (FIG. 8).

Here a third layer is added, the interconnection layer 20. The first, top layer 10 remains the same.

The second metal layer 12 as well, except there is no longer a connection track. The second layer 12 becomes a disk only for that electrode, completely covered by the first layer 10. No traces are sticking out.

Now a hole is made in the center of the second layer and penetrates the insulation layer to the other side. A via on this other side the connecting tracks are routed. And connect these to the via on one end and the electronics on the other end. And extra insulating layer will go below to sandwich the tracks.

In the shown embodiment, a single via 22 is formed through, the second layer 12 and the interconnection track 24 located in the interconnection layer 20.

Not shown is that a plurality of vias 22 may be formed through the second layer 12 and the interconnection track 24.

REFERENCES

10 First layer
12 Second layer
14 Base substrate
16 Electrically insulating layer
18 Electrically conductive and water non-permeable additional layer
20 Interconnection layer
22 Via(s)
24 Electrically conductive interconnection track
26 Insulating separation layer
100 Medical electrode

The invention claimed is:

1. A medical electrode, including:
a first layer made of a first material having a first electrochemical potential window and a first charge injection limit, and
at least one second layer made of a second material having a second electrochemical potential window and a second charge injection limit,
wherein the first layer and the second layer are located on a base substrate,
wherein the second electrochemical potential window is lower than the first electrochemical potential window,
wherein the first layer is provided on top of the second layer and encapsulates the second layer, so that no electrical current directly flows from the second layer toward a target tissue,
wherein the first layer is made of nanoporous reduced Graphene Oxide (rGO), and
wherein an electrically conductive and water permeable additional layer is interposed between the first layer and the second layer.

2. The medical electrode according to claim 1, wherein
an electrically insulating layer made of an electrically insulating material, an electrically insulating polymer material, is provided to cover the second layer while leaving the first layer exposed.

3. The medical electrode according to claim 1, wherein
the second layer is made of metal.

4. The medical electrode according to claim 1, wherein
the first layer is made of nanoporous reduced Graphene Oxide (rGO).

5. The medical electrode according to claim 4, wherein
an electrically conductive and water permeable additional layer is interposed between the first layer and the second layer.

6. The medical electrode according to claim 5, wherein
the electrically conductive and water permeable additional layer is made of graphene.

7. The medical electrode according to claim 6, wherein
the electrically conductive and water permeable additional layer includes a single layer of graphene or multiple layers of graphene.

8. The medical electrode according to claim 1, wherein
said medical electrode is implantable.

9. The medical electrode according to claim 1, wherein
said medical electrode is non-implantable.

10. A medical electrode arrangement, including:

a plurality of medical electrodes according to claim 1, and a connecting track made of an electrically conductive material for electrically connecting said plurality of medical electrodes.

11. The medical electrode arrangement according to claim 10, wherein the connecting track is encapsulated in an electrically insulating material.

12. The medical electrode arrangement according to claim 11, wherein said insulating material includes:

a dielectric film;

a ceramic layer;

a polymer layer, especially a parylene layer or a polyimide layer or a silicone layer or the like, or a combination thereof.

13. The medical electrode arrangement according to claim 10, wherein the connecting track is made of metal.

14. A medical electrode arrangement including:

a plurality of medical electrodes according to claim 1, and a connecting track made of an electrically conductive material for electrically connecting said plurality of medical electrodes, to electronic devices wherein at least one interconnection layer made of an electrically insulating material is sandwiched between the insulating separation layer and the base substrate, said interconnection layer covering the connecting track, and wherein at least one via is formed between the second layer and the interconnection track, for connecting the electrode to the connecting track.

15. A medical electrode arrangement according to claim 14, wherein the connecting track is made of metal.

16. The medical electrode according to claim 1, wherein the electrically conductive and water permeable additional layer is made of CVD graphene.

17. The medical electrode according to claim 1, wherein a connecting track made of metal extends through an electrically insulating layer and contacts the second layer of the medical electrode, wherein the second layer is a metal layer.

* * * * *